United States Patent [19]

Ferrari et al.

[11] 4,269,831
[45] May 26, 1981

[54] TOPICAL DERMATOLOGICAL METHOD OF USE OF AN ANDROSTENOPYRAZOLE

[75] Inventors: Richard A. Ferrari, Bethlehem; Arthur L. Beyler, North Greenbush, both of N.Y.

[73] Assignee: Sterling Drug Inc., New York, N.Y.

[21] Appl. No.: 37,439

[22] Filed: May 9, 1979

[51] Int. Cl.³ .............................................. A61K 31/58
[52] U.S. Cl. ................................................... 424/241
[58] Field of Search ........................................ 424/241

[56] References Cited

U.S. PATENT DOCUMENTS

| | | | |
|---|---|---|---|
| 3,704,295 | 11/1972 | Clinton | 260/239.55 D |
| 3,980,638 | 9/1976 | Babcock et al. | 260/239.5 |
| 4,039,669 | 8/1977 | Beyler et al. | 424/243 |

Primary Examiner—Elbert L. Roberts
Attorney, Agent, or Firm—Theodore C. Miller; B. Woodrow Wyatt

[57] ABSTRACT

A method of treating dermatological conditions associated with androgenic stimulatory influence which comprises applying to the affected skin area a composition comprising an antiandrogenically and glucocorticoidally effective amount of 17β-hydroxy-6α-methyl-17α-propynyl-4-androsteno[3,2-c]pyrazole in a pharmaceutical formulation suitable for topical application is disclosed.

1 Claim, No Drawings

TOPICAL DERMATOLOGICAL METHOD OF USE OF AN ANDROSTENOPYRAZOLE

BACKGROUND OF THE INVENTION

1. Field of the Invention

This invention relates to a method of treating dermatological conditions using 17β-hydroxy-6α-methyl-17α-propynyl-4-androsteno[3,2-c]pyrazole.

2. Description of the Prior Art

Certain dermatological conditions including acne and hirsutism are directly associated with androgenic stimulatory influences. One possible method of ameliorating these conditions is to counteract the androgenic stimulatory influence by the use of a substance possessing antiandrogenic activity (Beyler and Ferrari U.S. Pat. No. 4,039,669). Glucocorticoid substances are beneficial in treating more advanced cases of acne and have been used in the management of acne (Scholtz, Rational Drug Therapy, vol. 11, no. 7, pp. 1–6, 1977).

17β-Hydroxy-6α-methyl-17α-propynyl-4-androsteno[3,2-c]-pyrazole is known (Clinton U.S. Pat. No. 3,704,295, Example 89). The patent makes the following utility statements for the genus which includes 17β-hydroxy-6α-methyl-17α-propynyl-4-androsteno-[3,2-c]pyrazole (column 7):

Endocrinological studies of the steroido[3,2-c]-pyrazoles of the invention have shown that they possess useful metabolic, hormonal or anti-hormonal properties. In particular, they exhibit one or more of the following activities: anabolic, androgenic, pituitary inhibiting, estrogenic, progestational and adrenal cortical.

The steroido [3,2-c]pyrazoles of the invention, especially those having a saturated steroid nucleus and hydroxy and lower-alkyl radicals in the 17-position, further possess advantages in being anabolic (mytrophic and nitrogen retentive) at dose levels at which they do not show an appreciable degree of sex hormonal properties.

SUMMARY OF THE INVENTION

The invention relates to a method of treating dermatological conditions associated with androgenic stimulatory influence which comprises applying to the affected skin area a composition comprising an antiandrogenically and glucocorticoidally effective amount of 17β-hydroxy-6α-methyl-17α-propynyl-4-androsteno[3,2-c]pyrazole in a pharmaceutical formulation suitable for topical application.

DETAILED DESCRIPTION OF THE INVENTION INCLUSIVE OF THE PREFERRED EMBODIMENTS

17β-Hydroxy-6α-methyl-17α-propynyl-4-androsteno[3,2-c]-pyrazole has the following structural formula:

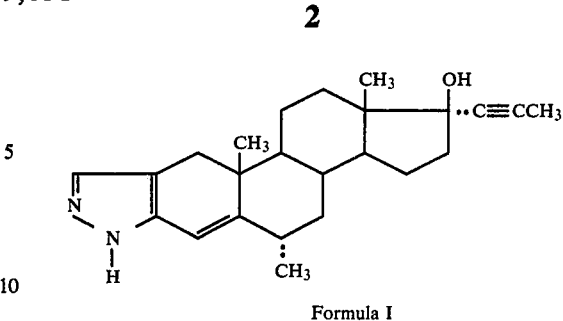

Formula I

The antiandrogenic and glucocorticoid properties of the compound of Formula I were shown by the following tests.

Topical Antiandrogenic Activity in Hamsters

Each flank organ of mature male Syrian golden hamsters having a mean initial body weight of 105 g. was medicated topically with the compound of Formula I dissolved in ethanol (5 microliters) for twenty-one days. Flank organ hair was clipped three times per week to facilitate application. On the day following the last medication the hamsters were killed with an overdose of sodium pentobarbital. The flank organ parameters and the weights of seminal vesicles, adrenals and thymus glands were determined. Flank organ diameter was measured parallel to the breadth of the hamster with vernier calipers. Wet weights were obtained on flank organs excised around the periphery of the pigmented area. The topical activity of the compound of Formula I was also compared with that of 17β-hydroxy-17α-propylandrost-4-en-3-one, an antiandrogen, and hydrocortisone. In this experiment the right flank organ was treated with the test compound while vehicle-treated left flank organ served as control. The overall flank organ development was scored on a scale of 0 to 4 (0, barely visible; 4, development comparable to that in the mature male). In addition, the individual characteristics of the flank organ, elevation (thickness relative to adjacent skin), area, hair pigment, skin pigment and hair growth were all scored separately on a scale of 0 to 4.

Results of the foregoing tests are shown in Tables I, II and III.

As shown by Table I the diameters and the wet weights of the flank organs were reduced at a dose of 5 micrograms per flank organ per day. No further reduction was observed at higher doses. At the highest dose (125 micrograms/flank organ/day) adrenal gland weights were significantly reduced but seminal vesicle and thymus weights were not significantly reduced. In a related experiment the compound of Formula I was found to be an effective inhibitor of androgen-stimulated flank organ parameters in mature female and castrated immature male hamsters without any systemic effects at doses ranging from 5 to 25 micrograms per flank organ.

In the comparison of 17β-hydroxy-17α-propyland-rost-4-en-3-one, hydrocortisone and the compound of Formula I shown by Table II, only the compound of Formula I produced a statistically significant inhibition of hamster flank organ development at 5 micrograms per day. The compound of Formula I had a flat dose response curve. At the 50 microgram dose 17β-hydroxy-17α-propylandrost-4-en-3-one inhibited flank organ diameter and development to a greater extent than the compound of Formula I, whereas hydrocortisone reduced only the weight of the flank organ. No changes in the parameters of the contralateral flank organ or other systemic activity were produced by any of the compounds in this test.

As shown by Table III 17β-hydroxy-17α-propylandrost-4-en-3-one caused a substantial reduction in the elevation, area, hair-pigmentation, skin-pigmentation and hair growth of the flank organ at 50 micrograms. Hydrocortisone caused a dramatic reduction in hair growth and practically no change in elevation, area and pigmentation of the flank organ. The compound of Formula I showed the combined effects of complete inhibition in hair growth and a modest inhibition in elevation and hair-pigmentation.

Systemic Antiandrogenic and Glucocorticoid Activity in Hamsters

A solution of the compound of Formula I in cottonseed oil was administered subcutaneously at 1 ml./kg. to castrated immature male Syrian golden hamsters having a mean initial body weight of 79 g. for 14 consecutive days concurrently with testosterone propionate. On the day following the last medication the hamsters were killed, the flank organ parameters were determined and the weights of seminal vesicles, adrenals and thymus glands were obtained.

The results of the foregoing test in Table IV show that the compound of Formula I has systemic antiandrogenic and glucocorticoid-like activity. The flank organ parameters were inhibited at the 5 mg./kg. dose. Final body weights and weights of seminal vesicles, adrenals and thymus glands were significantly less than those of androgen-treated controls.

Reduction and Hair Growth in Hamsters

The hair on the back of mature male Syrian golden hamsters having a mean initial body weight of 107 g. (7 hamsters per group) was removed with electric clippers. The vehicle (200 microliters of ethanol) or the test solution (0.02% or 0.1% of the compound of Formula I in ethanol) was pipetted slowly to cover the entire clipped area (9 cm.$^2$). After 30 daily applications, the hair was clipped from the same area and the hair clippings were collected and weighed in order to measure hair regrowth. The hair weights averaged 119±15 and 109±17 mg. for hamsters treated with 0.02% and 0.1% of the compound of Formula I, respectively, compared to 323±49 mg. for vehicle-treated hamsters.

In a second test all hair was clipped from the flank organs of 8 male Syrian golden hamsters having a mean body weight of 116 g. on the first day of the study. The hamsters were medicated daily with 5 microliters of ethanol on the left flank organ and 5 microliters of a 0.1% solution of the compound of Formula I in ethanol on the right flank organ for 14 consecutive days. On days 4, 8 and 12 each hamster was injected subcutaneously with 30 microcuries of $^{35}$S-cystine (0.72 nmole) dissolved in ethanol-saline (0.1 ml., 1:9, v/v). On day 15 several hairs were plucked from each flank organ. The hairs were exposed to X-ray film for 4 weeks. The distances between the radioactive sites and the hair resulting from the three pulses of $^{35}$S-cystine were measured and the daily rate of hair-growth was determined. As shown by Table V the rate of hair growth was reduced after 12 days of treatment.

Binding Competition in Hamster Flank Organs

The flank organs of twelve mature male Syrian golden hamsters each weighing from 120 to 140 g. and having been castrated 16-18 hours earlier were excised, dissected under the microscope to remove the dermis and the muscle layers and homogenized in buffer (1.5 volumes of 50 mM Tris, 0.5 mM mercaptoethanol and 0.1 mM ethylenediamine tetracetate, pH 7.4). The homogenate was centrifuged (120,000×g for 45 min.) and the cytosol was frozen and stored at −70° C. Six of the cytosol samples were thawed at room temperature, pooled and used for evaluation of in vitro binding. As shown by Table VI, when the cytosol was incubated with labeled dihydrotestosterone, the total binding of the labeled dihydrotestosterone was reduced by the addition of excess unlabeled dihydrotestosterone as well as by the compound of Formula I, thus showing competition of the compound of Formula I for the specific receptor sites.

Study in Guinea Pigs

The supracaudal glands of mature male guinea pigs having a mean initial body weight of 431 g. (8 guinea pigs per group) were medicated topically with a solution of the compound of Formula I (400 micrograms) in ethanol (10 microliters). Guinea pigs treated with ethanol served as controls. After 21 days of treatment the guinea pigs were killed and the areas of the supracaudal glands (pi×long radius×short radius) were measured in situ with calipers. The weights of seminal vesicles, adrenals and thymus glands were also measured. The average area of the supracaudal glands (72±6 sq. mm.) of the treated group was significantly ($p<0.01$) less than that of the control group (104±7 sq. mm.). No changes were observed in the weights of seminal vesicles, adrenals or thymus glands between the two groups.

Systemic Glucocorticoid Activity in the Rat

A solution of the compound of Formula I in ethanol-cottonseed oil (1:9, v/v) was administered orally to adrenalectomized Sprague-Dawley rats having a mean initial body weight of 188 g. (10 rats per group) for five consecutive days. Adrenalectomized rats receiving vehicle alone served as controls. Seven hours after the final medication the rats were killed and the thymus glands were excised and weighed. A portion of the liver was excised, frozen and digested in hot aqueous potassium hydroxide (30%). Liver glycogen was then determined. In this test the compound of Formula I caused thymolysis and liver glycogen deposition. The thymus weights at doses of 10 and 30 mg./kg. were 359±31 and 167±20 mg., respectively, in the medicated rats compared with 638±50 mg. in the control rats. The liver glycogen values at both dose levels (5.7±1.1 and 10.9±1.2 mg./kg., respectively) were significantly higher than those of the control group (1.82±0.03 mg./kg.).

Reduction in Hair Growth in Rats

Hair was clipped from the backs of male Sprague-Dawley rats, having a mean body weight of 300 g., three weeks after adrenalectomy. The clipped area (4 cm.×4 cm.) was medicated with approximately 500 microliters of 0.1% solution of the compound of Formula I, or hydrocortisone or 500 microliters of ethanol alone for a two-week pretreatment period. The clipped area was then depilated and the medication with either solution or ethanol alone was continued for 4 weeks. The density of hair growth was scored visually at weekly intervals and at termination of the experiment on a scale of 0 to 4 (0, no hair growth; 4, complete hair regrowth). Skinfold thickness was also measured using a micrometer at the end of the experiment, which was conducted blind.

The results of the foregoing test are shown in Table VII. In adrenalectomized rats the inhibitory effects of endogenous glucocorticoids on the hair cycle are removed and hair grows back in a uniform fashion. During the pretreatment period, hair regrowth was equivalent in all groups. During the four-week period after depilation the compound of Formula I inhibited hair growth for two weeks. After the fourth week, complete hair regrowth had occurred in the vehicle-treated rats, whereas hair growth was considerably less in the rats treated with the compound of Formula I. The effect of hydrocortisone was similar to that of the compound of Formula I. The skinfold thickness was also reduced by both compounds. The skin of the rats treated with the compound of Formula I was thinner (p<0.02) than that of those treated with hydrocortisone.

Conclusion

The foregoing results show that the compound of Formula I possesses both antiandrogenic and glucocorticoid properties, that its topical effects are a result of the combination of these two properties, and that it is active topically at doses at which it does not produce systemic effects.

FORMULATIONS

The compound of Formula I can be formulated as an ointment, cream, lotion, topical solution, paste, liniment, powder, aerosol or other dermatological preparation using the appropriate pharmaceutical vehicles and adjuncts.

TABLE I

Effect of Compound of Formula I on Mature Male Hamsters

| Topical Treatment µg Cpd. of Formula I/ flank organ/ day for 21 days | Flank Organ Diameter (mm) | Wet Weight (mg) | Organ Weights (mg) Adrenal | Thymus | Seminal Vesicles |
|---|---|---|---|---|---|
| Vehicle | 5.6$^a$ ±.2 | 45.3 ±2.1 | 25.7 ±0.7 | 55.6 ±2.2 | 312.1 ±16.5 |
| 1 | 5.7 ±.2 | 46.5 ±2.7 | 26.7 ±1.2 | 57.1 ±2.0 | 288.3 ±17.4 |
| 5 | 4.8$^b$ ±.2 | 36.4$^b$ ±2.2 | 25.5 ±0.5 | 53.2 ±1.7 | 277.6 ±22.4 |
| 25 | 4.7$^b$ ±.1 | 33.4$^c$ ±2.0 | 25.5 ±0.7 | 53.7 ±3.0 | 270.3 ±32.9 |
| 125 | 4.8$^b$ ±.2 | 30.7$^c$ ±1.6 | 21.0$^b$ ±1.1 | 52.8 ±3.4 | 267.3 ±21.6 |

$^a$Mean ± SE: n = 8
$^b$p < 0.1 compared to the mean of the vehicle-treated control group
$^c$p < .001 compared to the mean of the vehicle-treated control group

TABLE II

Effect of Topical Treatment of Compound of Formula I, 17β-Hydroxy-17α-propylandrost-4-en-3-one and Hydrocortisone on Mature Male Hamsters

| Topical Treatment$^a$ µg/RFO for 21 days | Development$^b$ LFO | RFO | Diameter$^c$ (mm) LFO | RFO | Weight$^c$ (mg) LFO | RFO |
|---|---|---|---|---|---|---|
| Vehicle | 4 (3-4) | 4 (3-4) | 5.7 ±.2 | 5.5 ±.2 | 41.7 ±3.8 | 43.5 ±1.8 |
| Cpd. of Formula I; 5 | 4 (3-4) | 3$^e$ (3-4) | 6.1 ±.1 | 5.2$^f$ ±.2 | 47.4 ±1.8 | 35.9$^d$ ±3.5 |
| Cpd. of Formula I; 50 | 4 (3-4) | 3$^e$ (3-4) | 6.0 ±.1 | 5.0$^f$ ±.1 | 49.2 ±2.7 | 33.2$^f$ ±1.1 |
| 17β-Hydroxy-17α-propyl-androst-4-en-3-one; 5 | 4 (3-4) | 3 (2-4) | 5.5 ±.1 | 4.9$^e$ ±.2 | 43.8 ±3.6 | 33.8$^d$ ±2.0 |
| 17β-Hydroxy-17α-propyl-androst-4-en-3-one; 50 | 4 (4) | 2$^f$ (1-2) | 5.8 ±.2 | 3.9$^f$ ±.2 | 45.7 ±1.9 | 21.4$^f$ ±1.2 |
| Hydrocortisone; 5 | 4 (4) | 4 (4) | 5.8 ±.2 | 5.7 ±.2 | 46.3 ±1.8 | 38.5$^e$ ±1.5 |
| Hydrocortisone; 50 | 4 (3-4) | 4 (3-4) | 5.8 ±.1 | 5.7 ±.1 | 45.9 ±1.3 | 39.1$^e$ ±1.7 |

$^a$All LFOs received vehicle. LFO, Left flank organ; RFO, Right flank organ: n = 7
$^b$Median score; Range in parentheses
$^c$Mean ± SE
$^d$p < .05 compared to vehicle treated LFO of same group
$^e$p < .01 compared to vehicle treated LFO of same group
$^f$p < .001 compared to vehicle treated LFO of same group

TABLE III

Effect of Topical Treatment of Compound of Formula I, 17β-Hydroxy-17α-propylandrost-4-en-3-one and Hydrocortisone on Hamster Flank Organ Development

| Topical Treatment$^a$ µg/Flank Organ for 21 days | Flank Organ (Mean Score) Elevation | Area | Hair Pigmentation | Skin Pigmentation | Hair Growth |
|---|---|---|---|---|---|
| LFO; vehicle | 3.3 | 3.9 | 3.7 | 3.6 | 3.4 |
| RFO; vehicle | 3.3 | 3.6 | 3.7 | 3.4 | 3.6 |
| LFO; vehicle | 3.6 | 4.0 | 3.7 | 3.6 | 3.6 |
| RFO; Cpd. of Formula I; 5 | 3.1 | 3.3 | 3.6 | 3.3 | 1.4 |
| LFO; vehicle | 3.3 | 4.0 | 3.4 | 3.6 | 3.3 |
| RFO; Cpd. of Formula I; 50 | 2.6 | 3.0 | 3.0 | 3.1 | 0 |
| LFO; vehicle | 3.3 | 3.9 | 3.7 | 3.9 | 3.3 |
| RFO; 17β-Hydroxy-17α-propylandrost-4-en-3-one; 5 | 2.6 | 3.1 | 3.3 | 4.0 | 3.1 |
| LFO; vehicle | 3.9 | 4.0 | 3.7 | 3.7 | 3.3 |
| RFO; 17β-Hydroxy-17α-propylandrost-4-en-3-one; 50 | 1.4 | 1.6 | 2.6 | 2.7 | 2.3 |
| LFO; vehicle | 3.7 | 4.0 | 3.7 | 4.0 | 3.9 |
| RFO; Hydrocortisone, 5 | 3.7 | 3.7 | 3.7 | 3.9 | 1.9 |
| LFO; vehicle | 3.6 | 4.0 | 3.1 | 3.4 | 3.4 |
| RFO; Hydrocortisone, 50 | 3.5 | 4.0 | 3.0 | 3.4 | 1.3 |

$^a$LFO, Left flank organ; RFO, Right flank organ: n = 7

TABLE IV

Effect of Subcutaneous Administration of the Compound of Formula I on Castrated Immature Male Hamsters

| Treatment mg/kg/day for 14 days sc Cpd. of Formula I | Testosterone Propionate | Final Body Weight | Flank Organ Diameter (mm) | Organ Weights (mg) | | | |
|---|---|---|---|---|---|---|---|
| | | | | Wet Weight (mg) | Seminal Vesicles | Adrenals | Thymus |
| 0 | 0 | 109[a] ±3 | 2.7 ±.1 | 6.5 ±.8 | 35 ±4 | 15.6 ±.5 | 67 ±5 |
| 0 | 0.4 | 106 ±3 | 4.3 ±.1 | 22.8 ±1 | 157 ±12 | 18.2 ±.7 | 58 ±7 |
| 2.5 | 0.4 | 99 ±2 | 4.0 ±.2 | 19.5 ±1 | 135 ±10 | 12.7[c] ±.3 | 28[b] ±3 |
| 5 | 0.4 | 93[b] ±3 | 3.6[c] ±.1 | 15.0[c] ±.7 | 107[b] ±12 | 12.3[c] ±.5 | 14[c] ±1 |

[a] Mean ± SE; n = 8
[b] p < .01 compared to the mean of the androgen-treated control group
[c] p < .001 compared to the mean of the androgen-treated control group

TABLE V

Effect of the Compound of Formula I on the Rate of Hair-Growth on Male Hamster Flank Organs

| Daily Topical Treatment | Rate of Hair Growth (mm/day) | |
|---|---|---|
| | First Interval (Day 4-8) | Second Interval (Day 9-12) |
| Left flank organ, vehicle | .535 ± .012[a] | .615 ± .005 |
| Right flank organ, 0.1% Compound of Formula I | .504 ± .014 | .566 ± .014[b] |

[a] Mean ± SE, n = 8
[b] p < .01 compared to the mean growth rate of left flank organ hair

TABLE VI

Binding Competition of the Compound of Formula I with $^3$H-Dihydrotestosterone (DHT) to Hamster Flank Organ Cytosol Receptor In Vitro

| Unlabelled Antagonist | Conc. (nM) | Molar Ratio Antagonist/Androgen | % Bound[a] (Mean ± SE) |
|---|---|---|---|
| None | — | | 13.96 ± .055 (3) |
| DHT | 20 | 10 | 7.95 ± .41[b] (3) |
| | 200 | 100 | 4.22 ± .001[b] (4) |
| | 2000 | 1000 | 4.00 ± .22[b] (3) |
| Compound of Formula I | 20 | 10 | 9.94 ± .45[b] (4) |
| | 200 | 100 | 8.55 ± .56[b] (4) |
| | 2000 | 1000 | 6.30 ± .003[b] (4) |

[a] Radioactivity bound to the cytosol protein in two hours calculated as a percentage of total 3H-dihydrotestosterone (2 nM) added to the incubation mixture. The values in parenthesis indicate number of assays
[b] p < .001 compared to the mean binding without antagonist

TABLE VII

Effect of Topical Treatment with 0.1% Compound of Formula I and Hydrocortisone on Hair-Growth in Male Adrenalectomized Rats

| Topical Treatment | Hair Growth Score[a] | | | | | | Skinfold Thickness[b] Treatment - mm (No. of Weeks) 4 |
|---|---|---|---|---|---|---|---|
| | Pretreatment (No. of Weeks) | | Treatment (No. of Weeks) | | | | |
| | 1 | 2 | 1 | 2 | 3 | 4 | |
| Vehicle | 1 (0-2) | 3 (1-4) | 0 (0-1) | 1 (0-2) | 3 (1-4) | 4 (3-4) | 2.51 ±.08 |
| Compound of Formula I | 1 (0-2) | 2.5 (0-4) | 0 (0-1) | 0 (0-1) | .5[d] (0-1) | 1[d] (0-3) | 1.82[d] ±.09 |
| Hydrocortisone | 2 (0-2) | 3 (1-4) | 0 (0) | 0[c] (0) | 1[c] (0-2) | 2[c] (0-4) | 2.11[d] ±.11 |

[a] Median score; Range in parenthesis, n = 12
[b] Mean ± SE, n = 12
[c] p < .01 compared to vehicle-treated control
[d] p < .001 compared to vehicle-treated control

We claim:

1. The method of treating dermatological conditions associated with androgenic stimulatory influence including acne and hirsutism which comprises applying to the affected skin area a composition comprising an antiandrogenically and glucocorticoidally effective amount equivalent to at least 5 micrograms per flank organ of a hamster of 17β-hydroxy-6α-methyl-17α-propynyl-4-androsteno[3,2-c]pyrazole in a pharmaceutical formulation suitable for topical application.

* * * * *